(12) United States Patent
James

(10) Patent No.: US 12,016,760 B2
(45) Date of Patent: Jun. 25, 2024

(54) INCONTINENCE TREATMENT SYSTEM AND METHODS OF USE

(71) Applicant: DIGNITY HEALTH, Phoenix, AZ (US)

(72) Inventor: Nicole James, Grass Valley, CA (US)

(73) Assignee: DIGNITY HEALTH, Phoenix, AZ (US)

( * ) Notice: Subject to any disclaimer, the term of this patent is extended or adjusted under 35 U.S.C. 154(b) by 1137 days.

(21) Appl. No.: 16/624,259

(22) PCT Filed: Jun. 26, 2018

(86) PCT No.: PCT/US2018/039592
§ 371 (c)(1),
(2) Date: Dec. 18, 2019

(87) PCT Pub. No.: WO2019/005865
PCT Pub. Date: Jan. 3, 2019

(65) Prior Publication Data
US 2021/0145656 A1    May 20, 2021

Related U.S. Application Data

(60) Provisional application No. 62/524,665, filed on Jun. 26, 2017.

(51) Int. Cl.
*A61F 13/495* (2006.01)
*A61F 13/56* (2006.01)

(52) U.S. Cl.
CPC ........ *A61F 13/495* (2013.01); *A61F 13/5644* (2013.01); *A61F 2013/4953* (2013.01)

(58) Field of Classification Search
CPC ............... A61F 13/495; A61F 13/5644; A61F 2013/4953
See application file for complete search history.

(56) References Cited

U.S. PATENT DOCUMENTS

| 2,703,577 | A | * | 3/1955 | May | A61F 13/505 604/401 |
| 3,895,629 | A | * | 7/1975 | Snyder | A61F 5/455 604/179 |
| 5,998,695 | A | * | 12/1999 | Roe | A61F 13/15 604/367 |

(Continued)

*Primary Examiner* — Guy K Townsend
(74) *Attorney, Agent, or Firm* — Booth Udall Fuller, PLC; Rodney J. Fuller

(57) ABSTRACT

Described herein is an incontinence treatment system and method of use. In certain embodiments the incontinence treatment system comprises a rear incontinence member capable of being releasably coupled to a front incontinence member. For example, in one certain embodiment the rear incontinence member includes a rear absorbent region, a rear outer layer coupled to the rear absorbent region, and a plurality of coupling members. The front incontinence member typically includes a front absorbent region and a front outer layer coupled to the front absorbent region, a support material being disposed around at least a portion of the front absorbent region, and one or more coupling regions being configured and arranged to engage at least a portion of the plurality of coupling members to couple the rear incontinence member to the front incontinence member.

19 Claims, 10 Drawing Sheets

(56) References Cited

U.S. PATENT DOCUMENTS

| | | | | |
|---|---|---|---|---|
| 6,018,093 A * | 1/2000 | Roe | A61F 13/495 | 604/367 |
| 6,372,952 B1 * | 4/2002 | Lash | A61F 13/53708 | 604/378 |
| 6,395,955 B1 * | 5/2002 | Roe | G01N 33/5308 | 604/362 |
| 6,551,295 B1 * | 4/2003 | Schmidt | A61F 13/5376 | 604/385.01 |
| 6,570,057 B1 * | 5/2003 | Schmidt | A61F 13/534 | 604/378 |
| 6,664,439 B1 * | 12/2003 | Arndt | A61F 13/15203 | 604/374 |
| 6,720,471 B1 * | 4/2004 | Arndt | A61F 13/53747 | 604/378 |
| 6,752,797 B2 * | 6/2004 | Oba | A61F 13/496 | 604/395 |
| 6,932,800 B2 * | 8/2005 | LaVon | A61F 13/15203 | 604/385.19 |
| 7,670,324 B2 * | 3/2010 | LaVon | A61F 13/49011 | 604/397 |
| 7,727,211 B2 * | 6/2010 | LaVon | A61F 13/505 | 604/397 |
| 7,772,455 B1 * | 8/2010 | Roe | A61F 13/51113 | 604/385.01 |
| 7,838,723 B1 * | 11/2010 | Schmidt | A61F 13/15203 | 604/385.01 |
| 11,083,644 B2 * | 8/2021 | Wciorka | A61F 13/536 | |
| 11,083,645 B2 * | 8/2021 | Wciorka | A61F 13/496 | |
| 11,134,925 B2 * | 10/2021 | Barnhorst | A61F 13/49017 | |
| 11,135,104 B2 * | 10/2021 | Barnhorst | A61F 13/49011 | |
| 2001/0053902 A1 * | 12/2001 | Roe | A61F 13/15 | 604/385.01 |
| 2002/0035354 A1 * | 3/2002 | Mirle | A61F 13/5146 | 604/385.01 |
| 2002/0091368 A1 * | 7/2002 | LaVon | A61F 13/15203 | 604/385.19 |
| 2007/0078420 A1 * | 4/2007 | Sugiyama | A61F 13/495 | 604/385.19 |
| 2012/0046634 A1 * | 2/2012 | Shields | A61F 13/622 | 604/391 |
| 2012/0209237 A1 * | 8/2012 | Paz | A61F 13/70 | 604/392 |
| 2012/0323195 A1 * | 12/2012 | Ehrnsperger | A61F 13/15 | 604/366 |
| 2013/0079740 A1 * | 3/2013 | Ehrnsperger | A61L 15/58 | 604/367 |
| 2013/0331806 A1 * | 12/2013 | Rosati | A61F 13/53743 | 604/366 |
| 2014/0005622 A1 * | 1/2014 | Wirtz | A61F 13/539 | 604/366 |
| 2014/0005623 A1 * | 1/2014 | Wirtz | A61F 13/53418 | 604/366 |
| 2014/0121487 A1 * | 5/2014 | Faybishenko | G16H 40/63 | 600/365 |
| 2015/0157251 A1 * | 6/2015 | Nelson | A61B 5/6808 | 600/580 |
| 2015/0282998 A1 * | 10/2015 | Arizti | A61F 13/51104 | 604/385.19 |
| 2017/0246052 A1 * | 8/2017 | Ludwig | A61F 13/15585 | |
| 2017/0252015 A1 * | 9/2017 | Barnhorst | A61F 13/42 | |
| 2017/0290715 A1 * | 10/2017 | Arizti | A61F 13/511 | |
| 2018/0228672 A1 * | 8/2018 | Wciorka | A61F 13/536 | |
| 2018/0228673 A1 * | 8/2018 | Wciorka | A61F 13/536 | |
| 2018/0228674 A1 * | 8/2018 | Wciorka | A61L 13/536 | |
| 2018/0369029 A1 * | 12/2018 | Barnhorst | A61F 13/51456 | |
| 2021/0145656 A1 * | 5/2021 | James | A61F 13/505 | |
| 2021/0386599 A1 * | 12/2021 | Barnhorst | A61F 13/495 | |
| 2022/0160336 A1 * | 5/2022 | Barnhorst | A61F 13/49017 | |
| 2022/0401272 A1 * | 12/2022 | Schneider | A61F 13/64 | |
| 2023/0063972 A1 * | 3/2023 | Barnhorst | A61F 13/622 | |

\* cited by examiner

INCONTINENCE TREATMENT SYSTEM AND METHODS OF USE

CROSS-REFERENCE TO RELATED APPLICATIONS

This application is the U.S. National Stage of International Application No. PCT/US2018/039592, filed on Jun. 26, 2018, which claims the benefit of U.S. Provisional Patent Application No. 62/524,665, filed on Jun. 26, 2017, the contents of each of which are incorporated herein by reference in their entireties.

FIELD

The embodiments provided herein relate to systems and methods of using an incontinence treatment device, such as a diaper. Specifically, certain embodiments advantageously provide a multi-part incontinence treatment device. The multi-part incontinence treatment device is designed so only a portion of the device, the soiled portion, is required to be replaced, without requiring the replacement of the whole device.

BACKGROUND

Absorbent articles such as diapers, training pants, or incontinence garments for adult, child, or infant, desirably provide a close, comfortable fit about the wearer and generally absorb and retain body exudates. It is well known that a wearer voids his or her bladder considerably more often than experiencing a bowel movement. Conventional absorbent articles, however, require removal of the entire piece, regardless whether the wearer voids his or her bladder or experiences a bowel movement. Thus, to address consumer's desire for generating less waste and protecting the environment, there is a need for absorbent articles that can be partially removed.

Removal of conventional absorbent articles also requires significant repositioning of the wearer. In the case of a larger wearer, such as a permanently or temporarily incontinent adult or a large child, the movement and repositioning of the wearer can create a burden on the caregiver, such as a nurse or a family member.

Some wearer of the absorbent article lacks the physical capacity to move him or herself, e.g., chair-bound, bed-bound, or incapacitated. Each time the wearer urinates; the caregiver is required to physically move the wearer to replace the absorbent article. The process creates significant physical stress on both the caregiver and the wearer. Under some circumstances, help must be sought from another person, such as a nurse, a family member, or caregiver, to turn the wearer from side to side to clean him/her and to change out the absorbent article. When such help is unavailable, the soiled absorbent article, and the urine or other exudates make an extended contact with the wearer. Thus, there is a need for replacing absorbent articles without significant reposition of an immobile wearer upon urination.

To that end, the inventor has provided a solution to extensive removal and replacement of entire absorbent articles upon only urination. The details of said innovation are contained herein. Absorbent articles such as diapers (adult or child/infant), training pants or incontinence garments desirably provide a close, comfortable fit about the wearer and generally absorb and retain body exudates.

SUMMARY

The present invention is directed to an incontinence treatment system and methods of use. In certain exemplary embodiments, the incontinence treatment system has a rear incontinence member capable of being releasably coupled to a front incontinence member. For example, in a particular embodiment the incontinence treatment system is directed to a rear incontinence member. The rear incontinence member typically has an rear absorbent region having a rear absorbent material, a rear outer layer coupled to the rear absorbent region, a rear waist region, and a crotch fastener coupled to a rear crotch region of the rear incontinence member. In this embodiment, the incontinence treatment system may further include a front incontinence member. The front incontinence member typically has a front absorbent region having a front absorbent material, a front outer layer coupled to the front absorbent region, a front waist region, and a crotch fastener coupled to a front crotch region of the front incontinence member. In a preferred embodiment the rear and front incontinence members have at least one or two rear waist couplers.

In another particular non-limiting embodiment, the incontinence treatment system comprises a rear incontinence member having a rear absorbent region, a rear outer layer coupled to the rear absorbent region, and one or more coupling members and a front incontinence member having a front absorbent region, a front outer layer coupled to the front absorbent region, a support material being disposed around at least a portion of the front absorbent region and one or more coupling regions being configured and arranged to engage at least a portion of the coupling members.

In yet another embodiment, the incontinence treatment system has (i) a rear incontinence member comprising a rear absorbent region having a rear absorbent material, a rear outer layer coupled to the rear absorbent region, a rear waist region having at least one rear waist coupler, and a rear crotch region of the rear incontinence member; (ii) a front incontinence member comprising a front absorbent region having a front absorbent material, a front outer layer coupled to the front absorbent region, a front waist region having at least one front waist coupler, and a front crotch region of the front incontinence member; and (iii) a crotch fastener operable to releasably couple the front crotch region of the front incontinence member to the rear crotch region of the rear incontinence member.

In yet another particular embodiment, the incontinence treatment system, has (i) a front incontinence member having a front waist region, a front crotch region, and a front absorbent region having a front absorbent material; (ii) a rear incontinence member having a rear waist region, a rear crotch region, and a rear absorbent region having a rear absorbent material; (iii) a first waist coupler operable to releasably couple a left portion of the front waist region to a left portion of the rear waist region; (iv) a second waist coupler operable to releasably couple a right portion of the front waist region to a right portion of the rear waist region; and (v) a crotch fastener operable to releasably couple the front crotch region of the front incontinence member to the rear crotch region of the rear incontinence member.

In different embodiments, the incontinence treatment system may be configured such that the support material (e.g., elastic material) is positioned within the front member and can be arranged to closely position the front absorbent region substantially adjacent to a crotch of a subject. By way of example only, the front member may be separately positioned adjacent to a crotch of a subject and the rear member may also be separately positioned adjacent to a posterior of the subject.

The incontinence treatment system may have many shapes that are suitable for a wearer, for example, rectangular, hourglass, and U-shape. In a particular aspect, the front incontinence member is the same or substantially similar to the shape and size of the rear incontinence member. For example, in this embodiment the front incontinence member is interchangeable with the rear incontinence member. In a non-limiting embodiment, the front crotch region maybe elasticized to contour the front crotch region to a subject's anatomy to provide greater protection against unwanted soiling.

The incontinence treatment system may further be configured so that the rear outer layer, the front outer layer, or both comprise one or more hydrophobic materials. For example, in a particular embodiment the incontinence treatment system comprises a hydrophobic dam, e.g., a hydrophobic surrounding at least two or three sidewalls of the front absorbent material in the front crotch region. The hydrophobic dam may extend beyond the front crotch region towards the front waist region. In a particular exemplary embodiment, the crotch fastener is coupled to the front crotch region and the rear crotch region abuts the crotch fastener, thereby operating as a barrier to define the amount the rear crotch region overlaps the front crotch region when the crotch fastener is coupled to the rear crotch region.

In another exemplary aspect, the rear absorbent region may further comprises a rear liquid-permeable layer such that at least half of the rear absorbent material is sandwiched between the rear liquid-permeable layer and the rear outer layer; the front absorbent region further comprises a front liquid-permeable layer such that at least half of the front absorbent material is sandwiched between the front liquid-permeable layer and the front outer layer; and each of the rear liquid-permeable layer and front liquid-permeable layer is adapted to contact the skin of a subject.

In certain further exemplary aspects of the invention, the rear incontinent member has a plurality of coupling members, wherein, at least a portion of the plurality of coupling members are positioned substantially adjacent to the rear absorbent region. As such, in this particular embodiment, the portion of the plurality of coupling members positioned adjacent to the rear absorbent region are configured and arranged to engage a region of the front member that is disposed substantially adjacent to the front absorbent region, which, in some embodiments, can couple together the front and rear members at a position substantially adjacent to the crotch of the subject. In other embodiments, the system may comprise additional coupling members configured to couple together the front absorbent region and the rear absorbent region and/or couple together outer layers of the front and rear members that are substantially adjacent to the front and rear absorbent members.

The present invention is also directed to a method of using an incontinence system on a subject. In certain particular embodiments, the subject is a patient that is substantially immobile. In this embodiment, the method may comprise the steps of: (i) providing a rear incontinence member comprising a rear absorbent region, a rear outer layer coupled to the rear absorbent region, a rear waist region, and a crotch region of the rear incontinence member; (ii) providing a front incontinence member comprising a front absorbent region, a front outer layer coupled to the front absorbent region, a front waist region, and a crotch region of the front incontinence member; (iii) providing a crotch fastener operable to releasably couple the front crotch region of the front incontinence member to the rear crotch region of the rear incontinence member; (iv) positioning the rear incontinence member on the subject so that the rear absorbent region is adjacent to a posterior of the subject and the rear waist region is substantially adjacent to hips of the subject with the rear crotch region positioned near or covering a transverse perineal muscle of the subject; (v) positioning the front incontinence member on the subject so that the front absorbent region covers the urethra of the subject and the front waist region is substantially adjacent to the hips of the subject; and (vi) coupling together the front crotch region to the rear crotch region by using the crotch fastener. In a particular non-limiting addition to this embodiment, the rear waist region of the rear incontinence member has a left side and a right side and the front waist region of the front incontinence member has a left side and a right side.

In this particular embodiment, the method further includes: (vii) providing a right side waist coupler operable to releasably couple the right side of the rear waist region to the right side of the front waist region; and (viii) providing a left side waist coupler operable to releasably couple the left side of the rear waist region to the left side of the front waist region; (ix) coupling the right side of the rear waist region to the right side of the front waist region by using the right side waist coupler; and (x) coupling the left side of the rear waist region to the left side of the front waist region by using the left side waist coupler.

Some embodiments may further provide uncoupling the front and rear members when the subject urinates, discarding the front member, and recoupling a new and unused front member to the already positioned rear member. Moreover, the method may also include uncoupling the front and rear members when the subject has a bowel movement, discarding the rear member, or the rear and front member, and positioning unsoiled front and rear members under the subject and coupling the rear and front members. In addition, in some embodiments, the front member may comprise a support material, such as, elastic, being disposed around at least a portion of the front absorbent region. For example, the support material may include an elastomer positioned within the front incontinence member, thereby positioning the front absorbent region adjacent to a urogenital anatomy of a subject.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
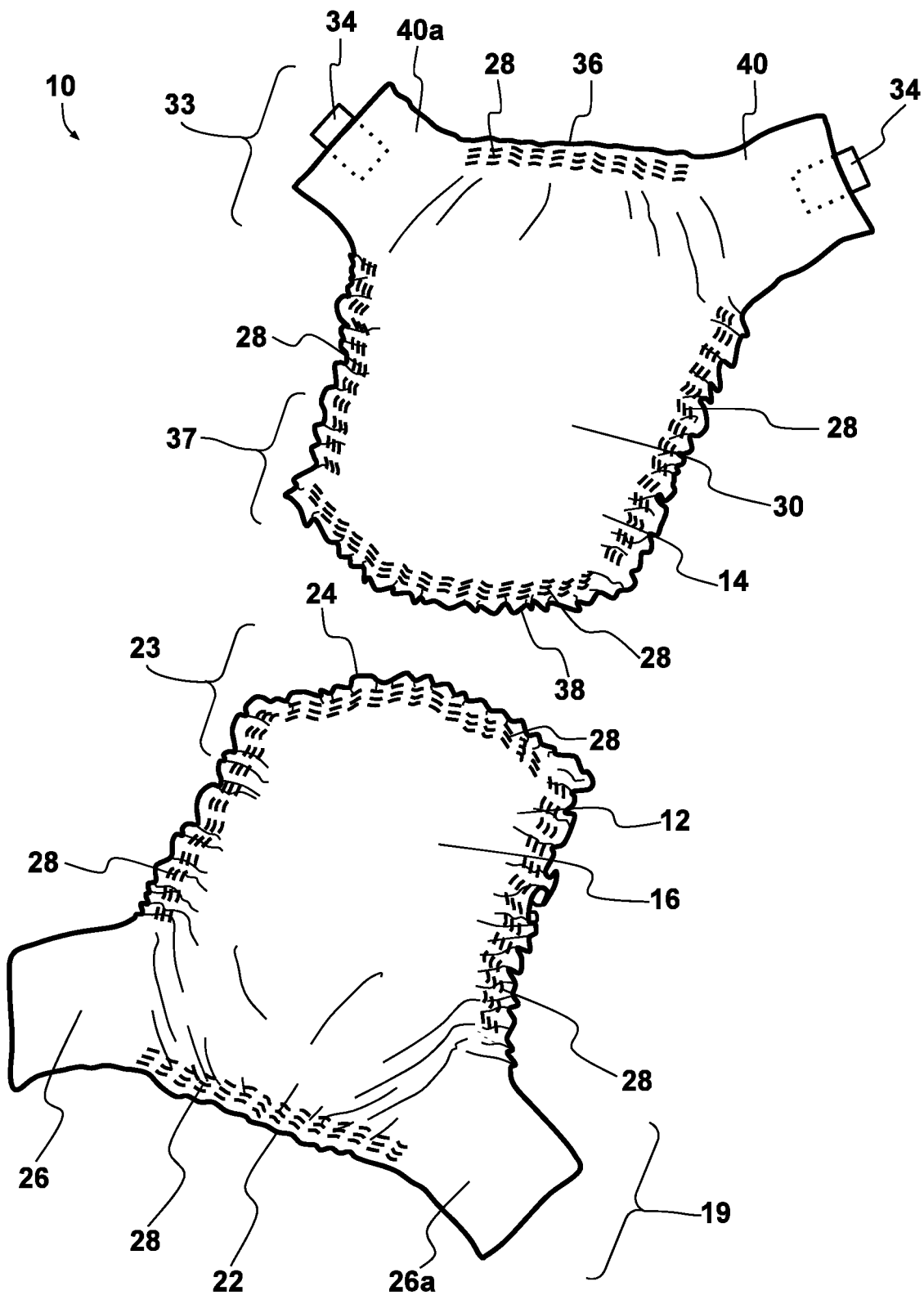
FIG. 1 provides a perspective view of an incontinence treatment system according to some embodiments.

Referring to the drawings, embodiments of an incontinence treatment system are illustrated and generally indicated as 10 in FIGS. 1-6B. In particular, the incontinence treatment system 10 can be generally used as an absorbent article to absorb, retain, and/or otherwise provide an article to retain one or more body exudates, such as urine, feces, menses, sweat, other discharges and fluids released in healthy or diseased states. Moreover, in some embodiments, the incontinence treatment system 10 can be used by any individual that is in need of an absorbent article, such as an infant, a toddler, a child, and/or an adult, including older individuals. By way of example only, some embodiments of the incontinence treatment system 10 can be employed by subjects that lack some or all mobility, such as an older person that is hospitalized or resides in a long-term care facility. As such, the incontinence treatment system 10 can be used for the substantially immobile individual to ensure that aspects of the system 10 are easily and readily changed by a caregiver (e.g., a nurse) to provide a dry environment around the area to which the system 10 is applied (e.g., a subject's crotch). Not every subject wearing the disclosed incontinence treatment system 10 needs to be a "patient" in a medical facility or home care, but subjects include any of a variety of healthy or unhealthy, mobile or immobile persons ranging in age from infants to the elderly.

As used herein, the terms "incontinent," "incontinence," or derivations and variations thereof is defined to include: unable to voluntarily control retention of urine or feces in the body; the inability of the body to control the evacuative functions of urination or defecation; partial or complete loss of bladder or bowel control; or lacks the mobility or mental capacity to reach a toilet or other body-exudate receptacle while retaining voluntary control retention of urine or feces. For example, a baby or a person who temporarily suffers from incontinence after undergoing surgery and/or is bedridden or otherwise lacks or has reduced mobility, thereby preventing him from reaching a toilet in a timely manner even though he has not lost his ability to voluntarily control retention of urine or feces in his body.

Referring now to FIGS. 1-6B, the incontinence treatment system 10 may comprise one or more constituent elements. For example, in some embodiments, the incontinence treatment system 10 may comprise a front member 12 that may be coupled to a rear member 14. In some aspects, the front member 12 may be releasably coupled to the rear member 14, as described in greater detail below. In other embodiments, the front member 12 can be largely irreversibly coupled to the rear member 14. Front member 12 may also be referred to herein as front incontinence member 12 and rear member 14 may also be referred to herein as rear incontinence member 14.

In some embodiments, the front member 12 can comprise a front absorbent region 16, a front outer layer 18, a front waist region 19 having a first end 22, and a front crotch region 23 having a second end 24. In some aspects, as illustrated in FIGS. 1-5, the first end 22 can longitudinally oppose the second 24. In certain embodiments, the front member 12 includes at least one coupling region 20 (see, FIGS. 4, 5, and 6B). By way of example only, the aforementioned elements of the front member 12 can be generally configured as a front portion of a generally conventional absorbent article (e.g., an adult diaper). In some aspects, the front absorbent region 16 can be coupled to and/or substantially integral with the front outer layer 18. In some embodiments, the front absorbent region 16 may comprise one or more materials that are capable of absorbing and retaining body exudates, such as urine or other fluids or semi-solids. For example, the front absorbent region 16 may comprise an outer fluid-permeable layer and an inner layer that absorbs and retains fluids such that the wearer/subject releases body exudates that can permeate and be retained within the front absorbent region 16. In some aspects, the front absorbent region 16 may comprise material such as woven or nonwoven natural (e.g., cotton or cellulose-derived materials), and/or non-natural fibers (e.g., polyester), or other hydrophilic materials. In some embodiments, due the to the positioning of the front absorbent region 16 in contact with the subject's genitals, the front absorbent region 16 can exhibit a substantially soft and non-abrasive material that provides comfort and support for the subject.

In some aspects, the front absorbent region 16 can be coupled to the front outer layer 18. In some embodiments, the front outer layer 18 can provide structural support for the front member 12 and can be used in coupling together the front and rear members 12, 14. In some embodiments, the front outer layer 18 can also comprise a substantially or completely liquid-impermeable configuration such that any body exudates absorbed by the front absorbent region 16 are not passed through the front outer layer 18 to contact that skin of the wearer/subject. In some embodiments, the front outer layer 18 may comprise liquid-impermeable and/or hydrophobic materials, such as, but not limited to polyethylene or may be coated with or laminated with polyolefins. Moreover, the front outer layer 18 can comprise a generally soft and non-abrasive material to avoid irritating the skin of the wearer/subject. As provided above, in some embodiments, the front absorbent region 16 and the front outer layer 18 can be generally coupled together. For example, the front absorbent region 16 can be coupled to the front outer layer 18 using conventional adhesives, sewing methodologies, or any other conventional method capable of coupling together these two elements. In other embodiments, the front absorbent region 16 can be integral with the front outer layer 18.

Figure 2:
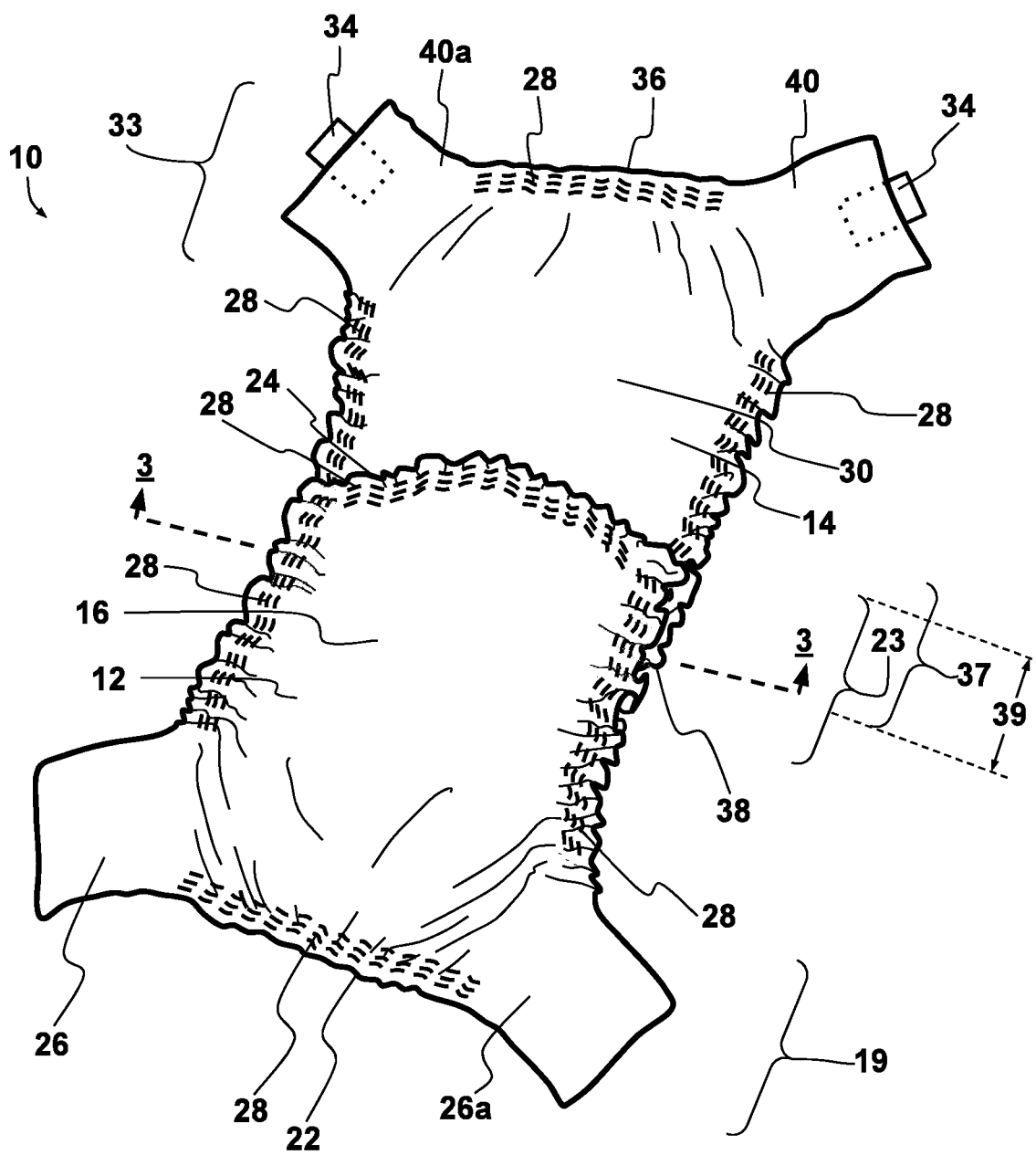
FIG. 2 provides a perspective view of an incontinence treatment system according to some embodiments.
Figure 3:
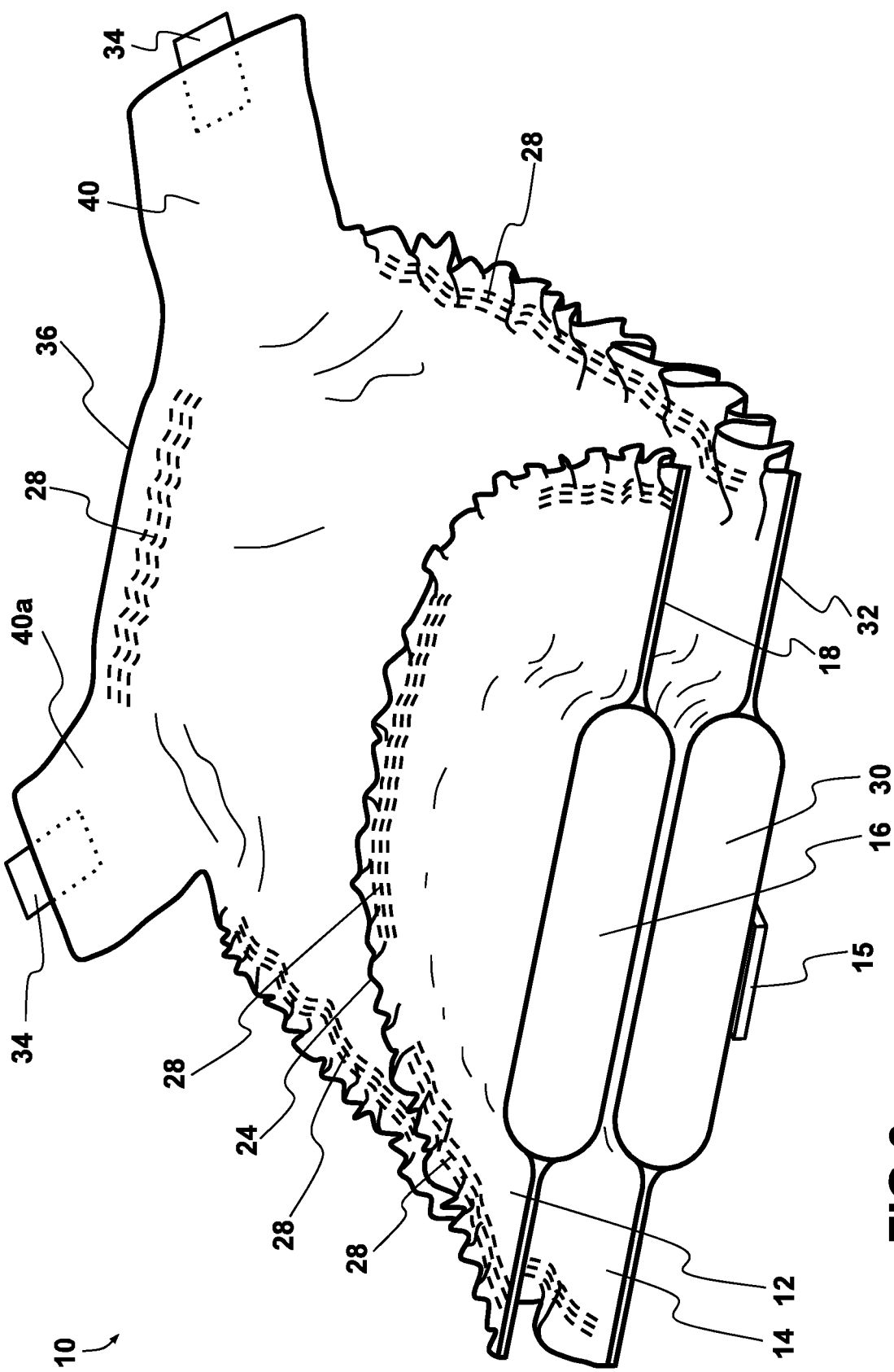
FIG. 3 provides a cross-sectional perspective view of the incontinence treatment system of FIG. 2.
Figure 4:
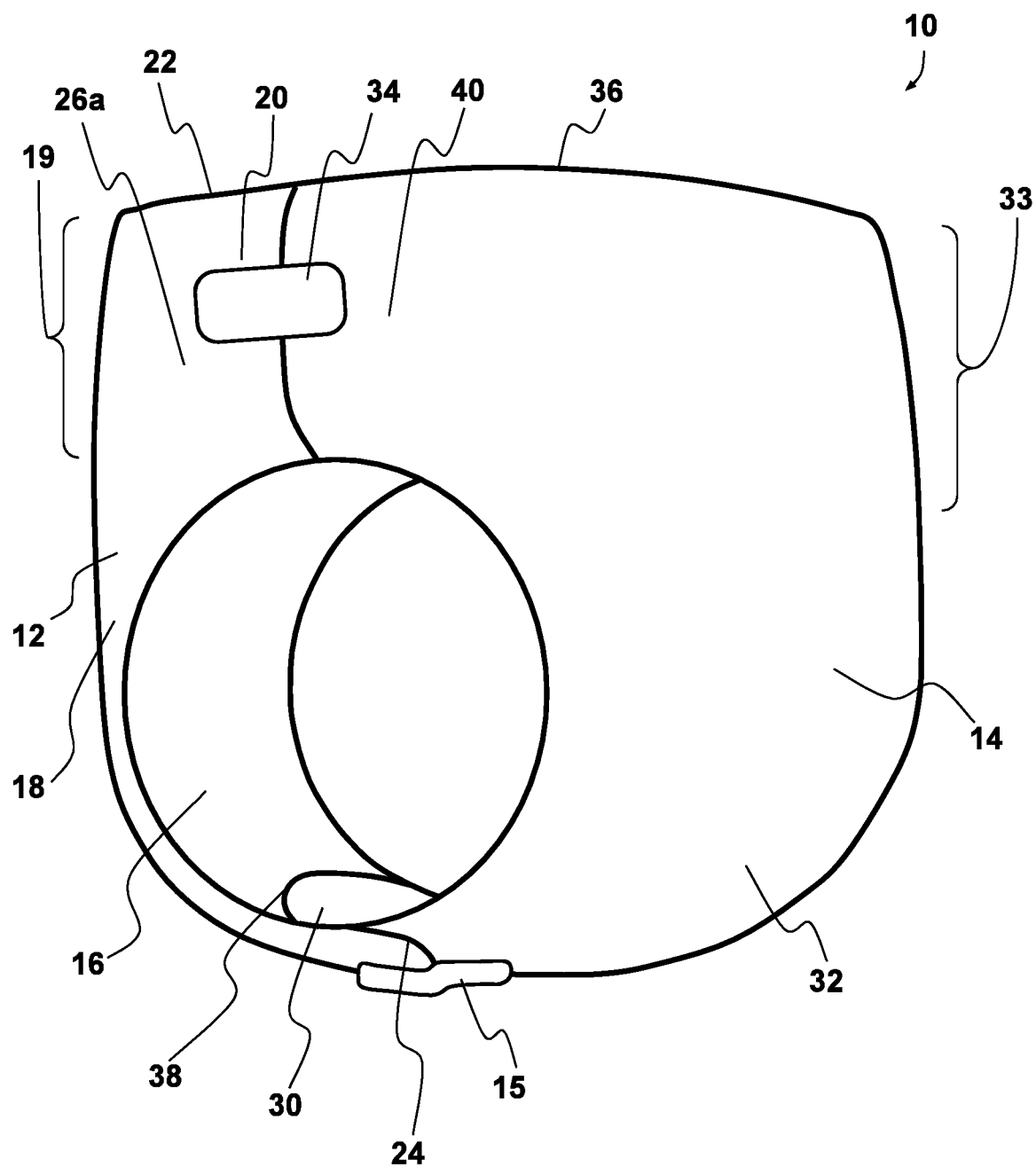
FIG. 4 provides a side perspective view of an incontinence treatment system according to some embodiments.

In some embodiments, at least a portion of the front member 12 can comprise a support material 28, as illustrated in FIGS. 1-3. For example, in some embodiments, the support material 28 can comprise elastic, elastomeric or another material that can impart support and structural flexibility to one or more aspects of the front member 12 and/or rear member 14. In some aspects, the support material 28 can be coupled to and/or immediately adjacent to the front absorbent region 16. As such, the front absorbent region 16 can be provided an element of structural stability to closely engage the genitalia of the wearer/subject to provide close contact between the genitalia and the front absorbent region 16. Moreover, in some embodiments, the support material 28 can be positioned throughout the front and rear members 12, 14 to provide structure and support throughout the incontinence treatment system 10 (e.g., to closely engage legs of the wearer/subject when the incontinence treatment system 10 is in place around the waist/crotch of the patient). In some embodiments, the support material 28 can be positioned in the front waist region 19 and/or a rear waist region 33. In certain embodiments, the support material 28 can be positioned in the front crotch region 23 and/or second end 24 of the front member 12. In various embodiments, the support material 28 can be positioned in a rear crotch region 37 and/or a second end 38 of the rear member 14. In some embodiments, the support material 28 can be positioned along at least a portion of the sides of the front absorbent region 16 between the first end 22 and the second end 24 of the front member 12. In numerous embodiments, the support material 28 can be positioned along at least a portion of the sides of the rear absorbent region 30 between a first end 36 and the second end 38 of the rear member 14.

Referring now to FIGS. 1-6B, the rear member 14 can comprise a rear absorbent region 30, a rear outer layer 32, the rear waist region 33 having a first end 36, and a rear crotch region 37 having a second end 38. In some embodiments, the rear member 14 also includes at least one coupling member 34. By way of example only, the aforementioned elements of the rear member 14 can be generally configured as a rear portion of a generally conventional absorbent article (e.g., an adult diaper). The rear member 14 cups or at least partially covers the buttocks or posterior of the wearer/subject. In some aspects, the rear absorbent region 30 can be coupled to and/or substantially integral with the rear outer layer 32. In some embodiments, the rear absorbent region 30 may comprise one or more materials that are capable of absorbing and retaining body exudates, such as urine or other fluids or semi-solids. For example, the rear absorbent region 30 may comprise an outer fluid-permeable layer and an inner layer that absorbs and retains fluids such that the wearer/subject releases body exudates that can permeate and be retained within the rear absorbent region 30. In some aspects, the rear absorbent region 30 may comprise material such as woven or non-woven natural (e.g., cotton or cellulose-derived materials), and/or non-natural fibers (e.g., polyester), or other hydrophilic materials. In some embodiments, due the to the positioning of the rear absorbent region 30 substantially adjacent to the subject's anus 82, the rear absorbent region 30 can exhibit a substantially soft and non-abrasive material that provides comfort and support for the subject. Put another way, the rear absorbent region 30 can be substantially similar to or the same as the front absorbent region 16.

In some aspects, the rear absorbent region 30 can be coupled to the rear outer layer 32. In some embodiments, the rear outer layer 32 can provide structural support for the rear member 14 and can be used in coupling together the front and rear members 12, 14. In some embodiments, the rear outer layer 32 can also comprise a substantially or completely liquid-impermeable configuration such that any body exudates absorbed by the rear absorbent region 30 are not passed through the rear outer layer 32 to contact that skin of the wearer/subject. In some embodiments, the rear outer layer 32 may comprise liquid-impermeable and/or hydrophobic materials, such as, but not limited to polyethylene or may be coated with or laminated with polyolefins. Moreover, the rear outer layer 32 can comprise a generally soft and non-abrasive material to avoid irritating the skin of the wearer/subject. Put another way, the rear outer layer 32 can be substantially similar to or the same as the front outer layer 18.

As provided above, in some embodiments, the rear absorbent region 30 and the rear outer layer 32 can be generally coupled together. For example, the rear absorbent region 30 can be coupled to the rear outer layer 32 using conventional adhesives, sewing methodologies, or any other conventional method capable of coupling together these two elements. In other embodiments, the rear absorbent region 30 can be integral with the rear outer layer 32.

Figure 5:
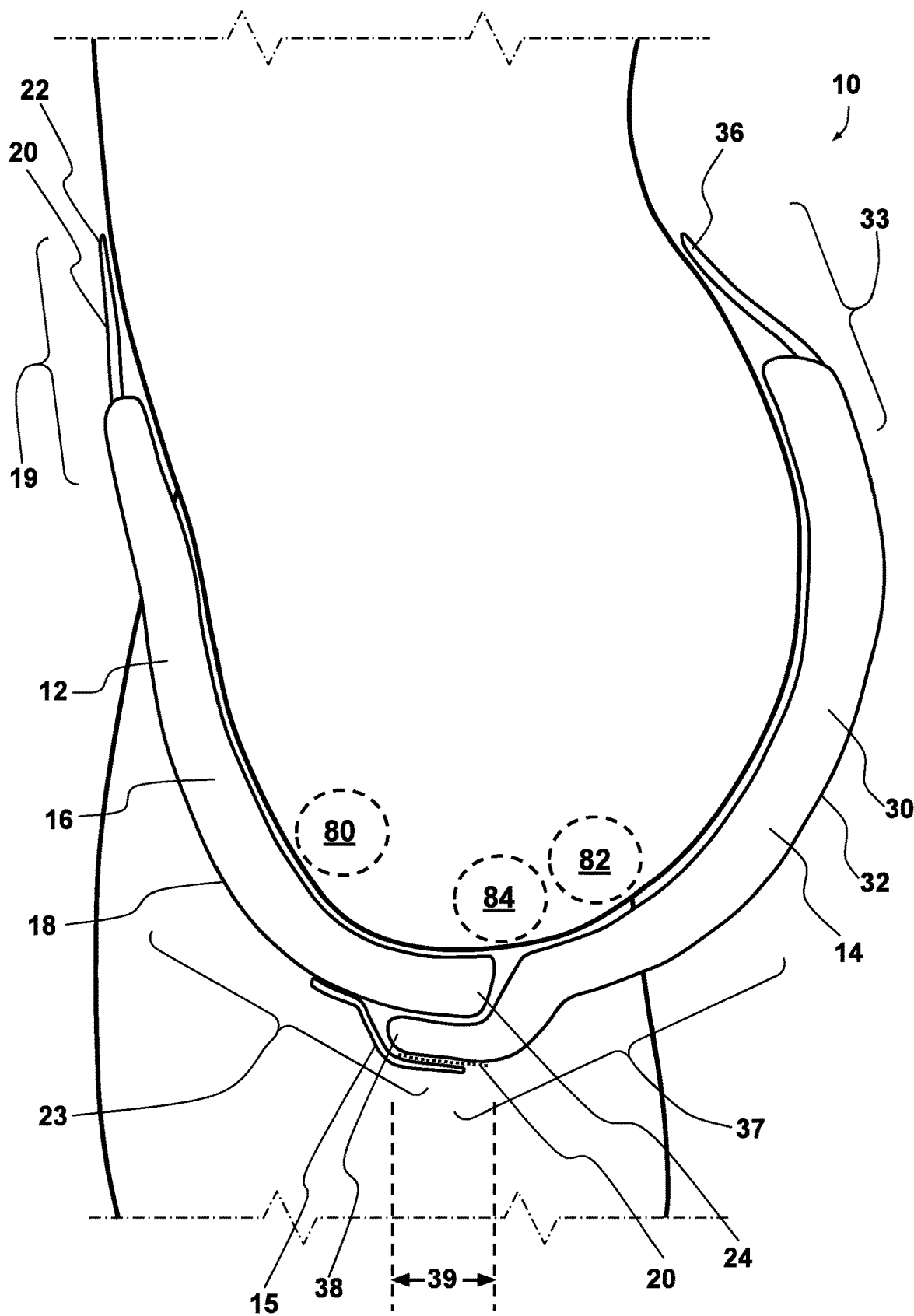
FIG. 5 provides a cross-sectional view of a subject wearing an incontinence treatment system according to some embodiments.

FIG. 5 illustrates a cross-sectional view of the incontinence treatment system 10 worn by a subject to assist in showing the relative positions of elements of the incontinence treatment system 10. In some embodiments, the incontinence treatment system 10 includes a crotch fastener 15 to releasably couple front crotch region 23 of the front member 12 to the rear crotch region 37 of the rear member. The front member 12 covers at least the urethra 80 of the subject so that the front absorbent region 16 collects exudates when the subject voids his or her bladder. The rear member 14 covers at least the anus 82 of the subject so that the rear absorbent region 30 collects feces. In some embodiments, the point where the front crotch region 23 meets the rear crotch region 37 is near or below a transverse perineal muscle 84 of the subject (e.g., within 2 cm, 3 cm, 4 cm, or 5 cm of being directly beneath, relative to axis of the subject's body, a transverse perineal muscle 84 when the subject is in a reclining position). Thus, ignoring any amount of overlap 39 (e.g., where rear crotch region 37 overlaps over part of front crotch region 23), the second end 24 of front member 12 desirably meets the second end 38 of rear member 14 near or below a transverse perineal muscle 84 of the subject.

Figure 6A:
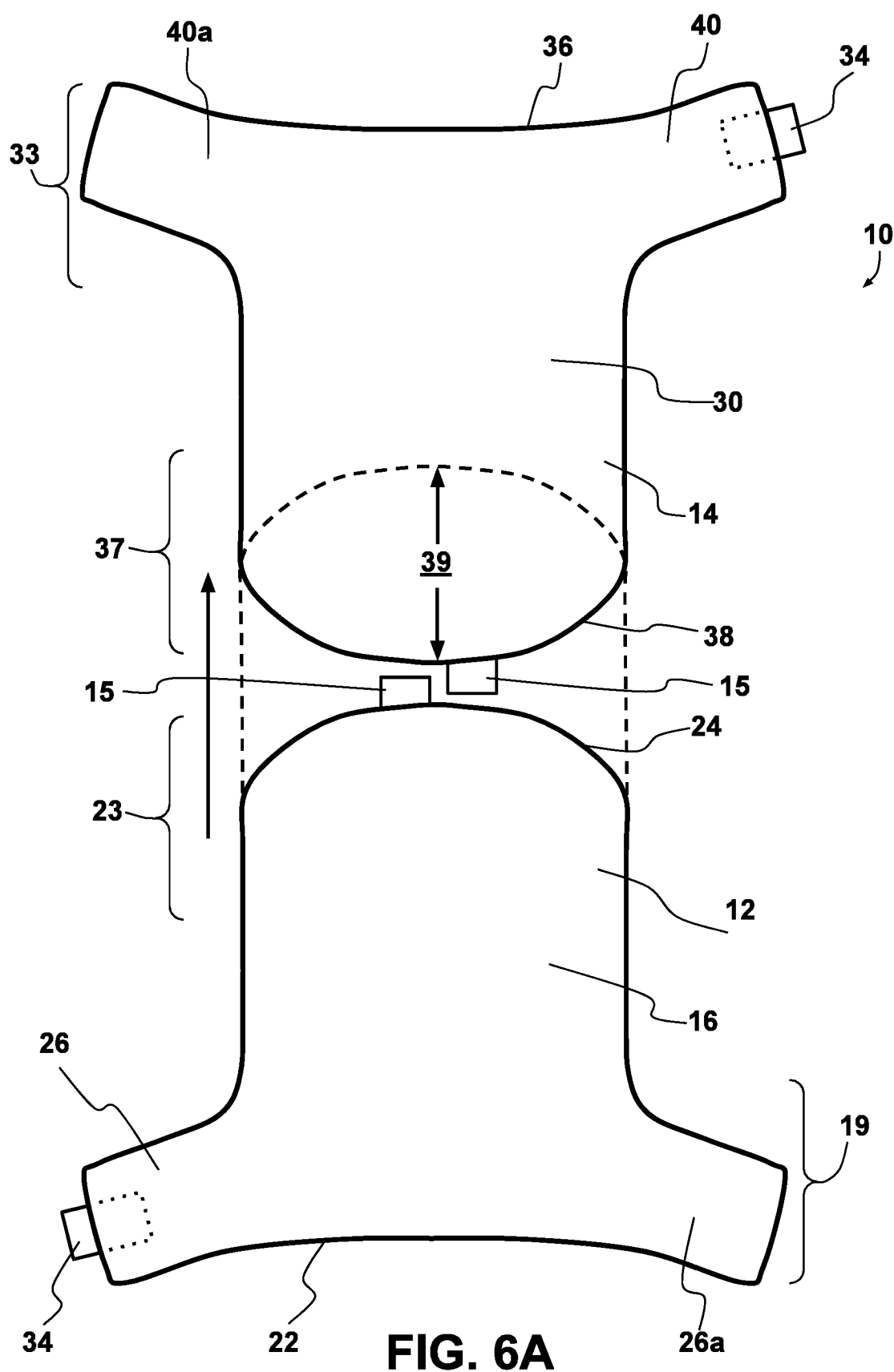
FIGS. 6A and 6B provide top-down plan views of a front and back of an incontinence treatment system according to some embodiments.
Figure 6B:
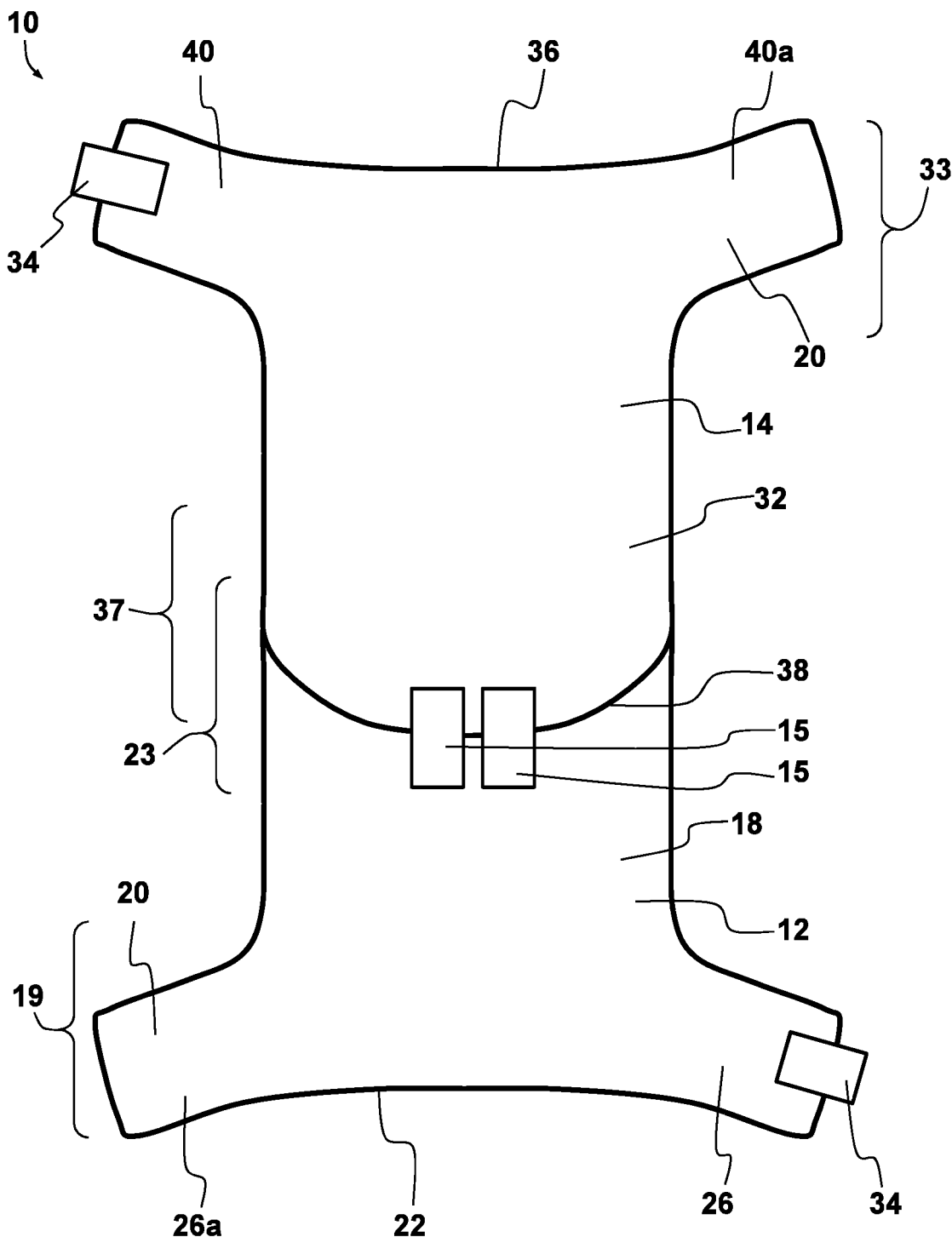

According to some embodiments, a portion of the rear crotch region 37 overlaps a portion of the front crotch region 23 when the front member 12 is coupled to the rear member 14. The amount of overlap 39 is depicted as the overlap at a medial or central portion of the rear crotch region 37 and the front crotch region 23, as illustrated in FIGS. 5-6B. FIG. 6A illustrates a plan view towards the front and rear absorbing regions 16, 30, before the crotch fastener 15 has coupled the front and rear members 12, 14 together. FIG. 6B illustrates a plan view towards the front and rear outer layers 18, 32, after the crotch fastener 15 have coupled the front and rear members 12, 14 together. In some embodiments, the length of overlap 39 is at least: 1 cm, 1.5 cm, 2 cm, 2.5 cm, 3 cm, 4 cm, or 5 cm. In certain embodiments, the length of overlap 39 is between: 0.5-12 cm, 0.5-8 cm, 0.5-7 cm, 1-6 cm, 1-4 cm, 2-12 cm, 2-7 cm, or 3-12 cm. In numerous embodiments, the rear crotch region 37 overlaps over part of the front crotch region 23 (see, FIG. 5), thereby allowing the front absorbent region 16 to cup the urogenital region of the subject better than if the front crotch region 23 were to overlap part of the rear crotch region 37. In some embodiments, the placement of the crotch fastener 15 determines the amount of overlap 39 by operating as a barrier to prevent overlap 39 beyond a predetermined point.

Figure 7A:
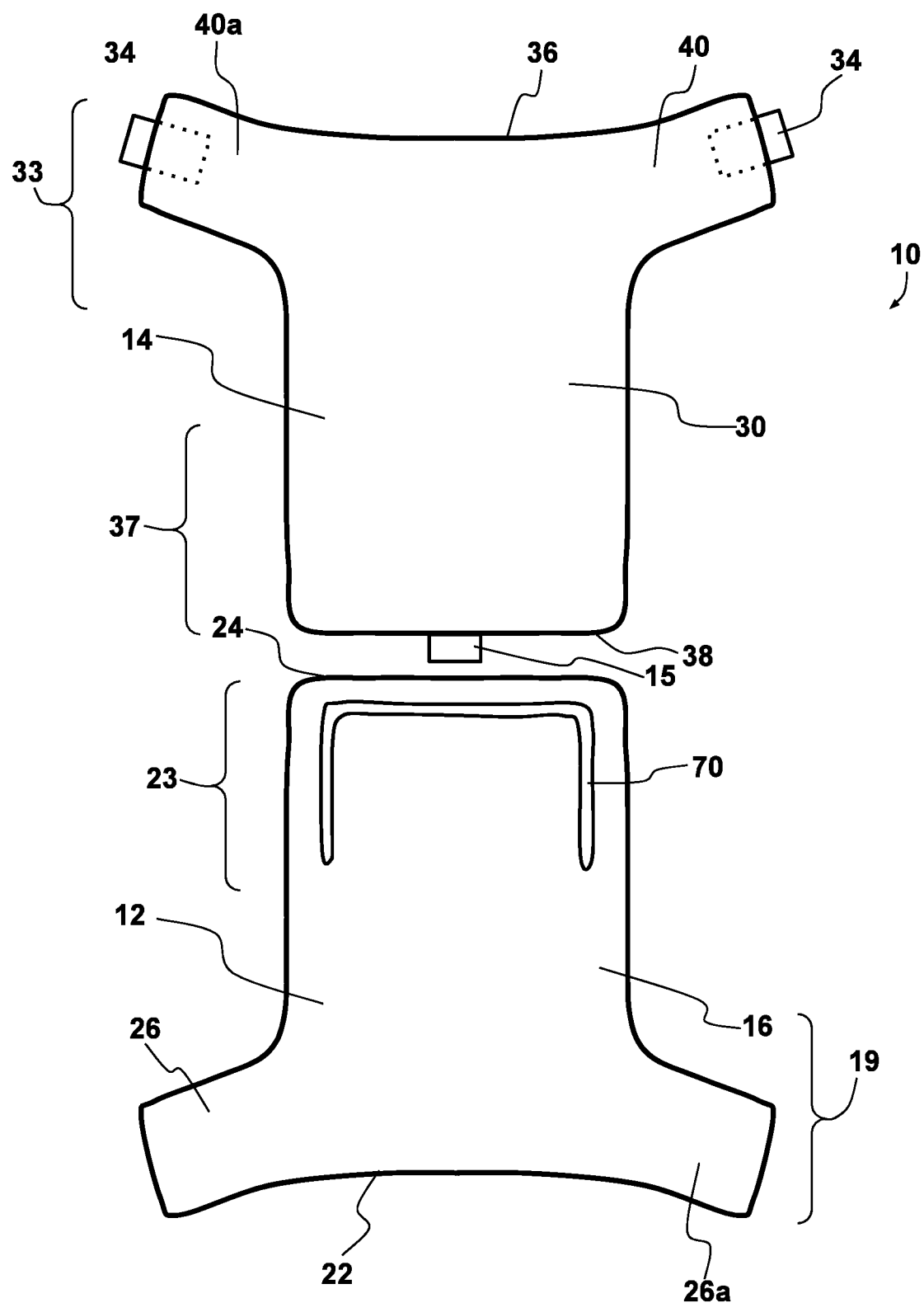
FIG. 7A provides a top-down plan view of an incontinence treatment system according to some embodiments.
Figure 7B:
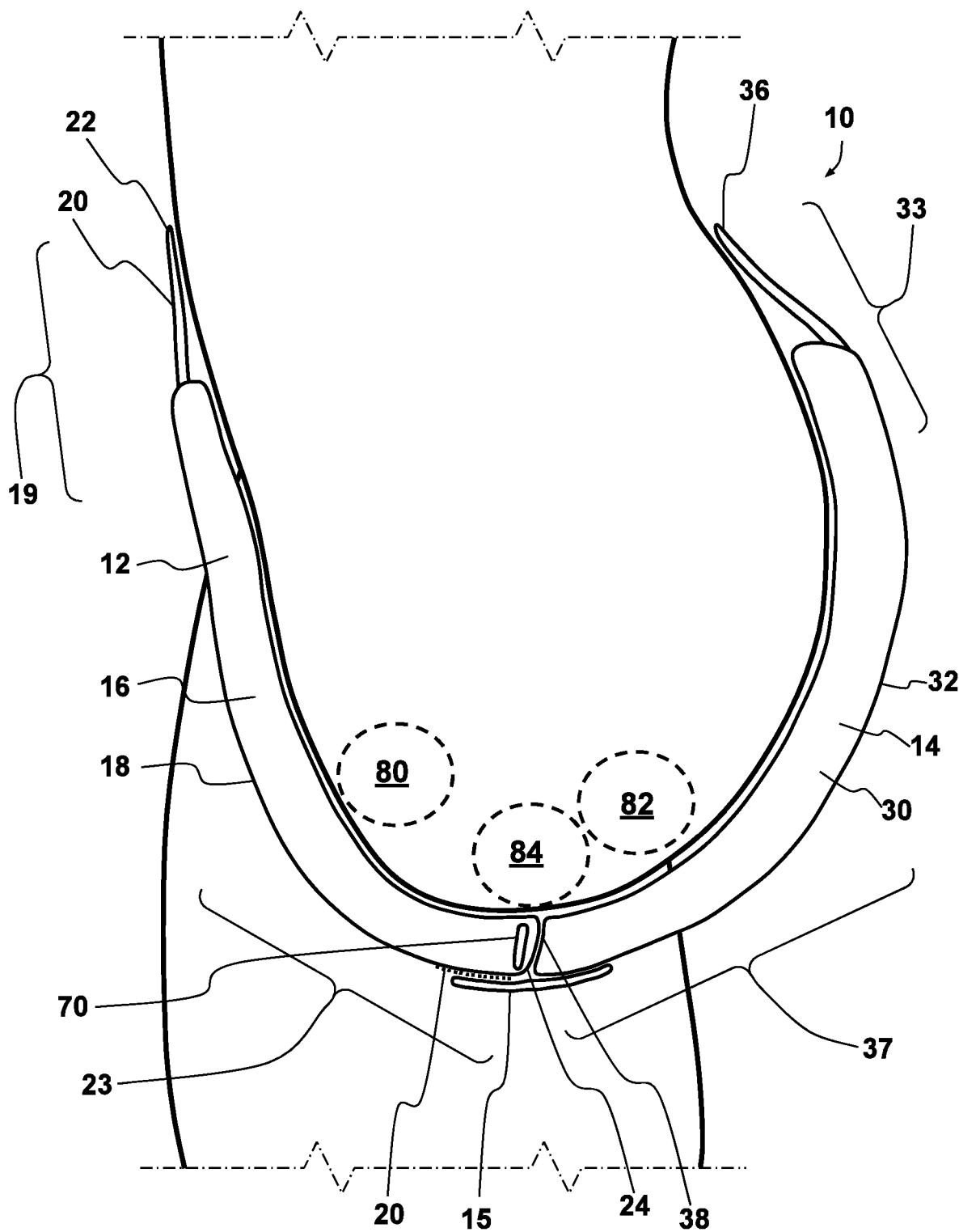
FIG. 7B provides a cross-sectional view of a subject wearing the incontinence treatment system of FIG. 7A.

In certain embodiments, neither the front crotch region 23 nor the rear crotch region 37 overlap one another where the crotch fastener couples the front and rear members 12, 14 together, as illustrated in FIGS. 7A and 7B. In this case, the second end 24 and second end 38 are sized and shaped to conformally meet so there is no overlap. FIG. 7B shows a non-limiting example where second end 24 and second end 38 are both straight so that they may meet and join flush generally below a transverse perineal muscle 84 of the subject (see, FIG. 7B).

In various embodiments, a hydrophobic dam or wall 70 circumscribes at least a portion of the side edges of the front absorbent region 16, as illustrated in FIGS. 7A and 7B. Wall 70 helps to contain liquids and body exudates within front absorbent region 16 and reduce leakage of liquid from the front absorbent region 16 into the rear member 14. The wall 70 circumscribes the side edges of the front absorbent region 16 at least along the second end 24 and partially up into the front crotch region 23.

In some embodiments, the front member 12 is sized and shaped the same as the rear member 14. In certain embodiments, the front member 12 is identical to the rear member 14 ("identical" meaning they are generally the same size and shape and contain the same elements in the same locations and ignoring the fact that manufacturing variations and tolerances may introduce differences). In some embodiments, the front member 12 and the rear member 14 are interchangeable within the incontinence treatment system 10. For example, FIGS. 6A and 6B illustrate a non-limiting embodiment where the front member 12 and the rear member 14 are interchangeable, are sized and shaped the same, and/or are substantially identical to each other.

In some embodiments, the incontinence treatment system 10 includes the crotch fastener 15 to releasably couple the front member 12 and the rear member 14 together around the crotch of a wearer or subject (e.g., the incontinence treatment system 10 wraps around the subject's urogenital region and anus 82, but not the entirety of the subject's waist). For example, support material 28 within front member 12 and/or rear member 14 provide sufficient conformal tension on the crotch of the wearer/subject when the crotch fastener 15 couples the front member 12 and rear member 14 together that wrapping entirely around the waist of the wearer/subject is unnecessary.

In numerous embodiments, the incontinence treatment system 10 includes at least one crotch fastener 15 and at least one coupling member 34 to releasably couple the front member 12 and the rear member 14 together around the crotch and waist of a wearer or subject. The crotch fastener 15 and coupling member 34 can each releasably couple two separate members together. Each crotch fastener 15 and coupling member 34 includes an adhesive, adhesive tape, snap, hook and loop fastener (e.g., VELCRO®), coupler, clasp, band, elastomeric band, clamp, belt, connector, tie, or any other material or apparatus (existing now or yet to be developed) that is capable of coupling together the front and rear members 12, 14. Fasteners and couplers discussed herein are used interchangeably and are not intended to signify that a fastener is different than a coupler. For example, the structure and function of a crotch fastener 15 may be the same as a coupling member 34, with the only difference being that the crotch fastener 15 couples in a different location on the incontinence treatment system 10 than the coupling member 34. The crotch fastener 15 and coupling member 34 can be releasably coupled to each of the two sides it is coupling together, or releasably coupled to one side while the other side is affixed or otherwise irreversibly attached to the crotch fastener 15/coupling member 34.

Figure 8:
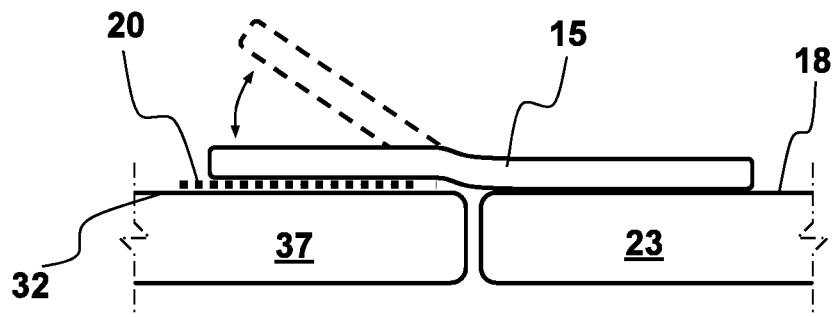
FIG. 8 provides a side cross-sectional view of a coupler or fastener for various embodiments of an incontinence treatment system.
Figure 9A:
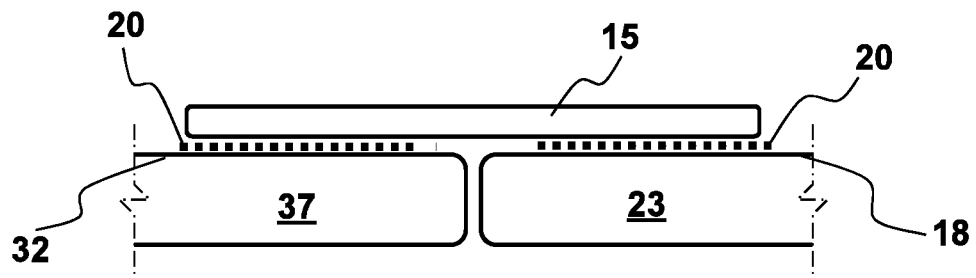
FIGS. 9A-9C provide cross-sectional views of a coupler or fastener for various embodiments of an incontinence treatment system.
Figure 9B:
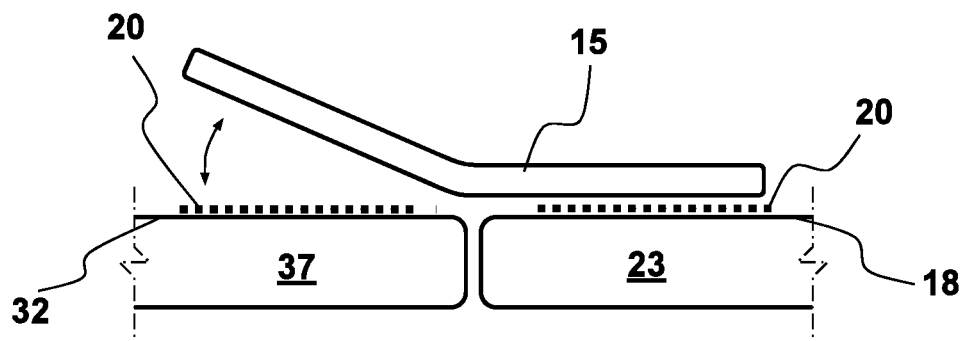
Figure 9C:
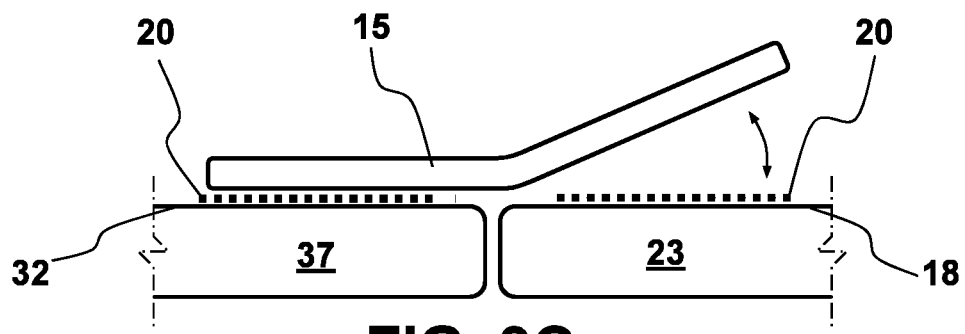

Referring to FIGS. 8 and 9A-9C, in various embodiments the crotch fastener 15 and the coupling members 34 can be any one of a variety of releasable couplers. Because the crotch fastener 15 and the coupling members 34 are releasable couplers in numerous embodiments, a crotch fastener 15 or coupling member 34 can be releasably coupled to both sides of the coupling or releasably coupled to only one side of the coupling (i.e., securely affixed to one side and releasably coupled to the other side). FIGS. 8 and 9A-9C illustrate cross-sectional views of a non-limiting example of coupling crotch fastener 15 to the front member 12 and rear member 14. In FIG. 8, the crotch fastener 15 is affixed to the front crotch region 23 of front member 12 (e.g., at or near second edge 24) but releasably coupled to the rear crotch region 37 of rear member 14 (e.g., at or near second edge 38). For example, coupling region 20 shown in FIG. 8 may comprise the loop portion of a hook and loop fastener comprising the crotch fastener 15 allowing the crotch fastener 15 to be releasably lifted away from the surface of the coupling region 20 and the rear outer layer 32 (see, arrow in FIG. 8). In an alternative embodiment, the crotch fastener 15 may be releasably coupled to the front crotch region 23 of front member 12 (e.g., at or near second edge 24) while being affixed to the rear crotch region 37 of rear member 14 (e.g., at or near second edge 38). In FIGS. 9A-9C, the crotch fastener 15 is releasably coupled to both the front crotch region 23 (e.g., at or near second edge 24) and the rear crotch region 37 (e.g., at or near second edge 38). Thus, the crotch fastener 15 is: capable of being releasably lifted away from the rear outer layer 32 of rear member 14 (see, arrow in FIG. 9B); or capable of being releasably lifted away from the front outer layer 18 of front member 12 (see, arrow in FIG. 9C). While the coupling region 20 shown in FIGS. 8 and 9A-C generally depict a hook and loop type fastener used as the crotch fastener 15, the crotch fastener 15 may be any one of a variety of different fasteners or couplers, including, adhesive, adhesive tape, or other couplers or fasteners described herein. Even though FIGS. 8 and 9A-C show a non-limiting example of a crotch fastener 15, these same figures and corresponding detailed description also apply equally to the coupling members 34, thus describing numerous variations for a coupling member 34 to couple a portion of the front member 12 (e.g., front waist region 19) to a portion of the rear member 14 (e.g., rear waist region 33).

Referring again generally to FIGS. 1-6B, in some embodiments, the front member 12 can comprise at least one coupling region 20 within or near the front waist region 19. Specifically, in some aspects, the front outer layer 18 can comprise the coupling region 20. For example, the front member 12 can comprise the first end 22 generally in or near the front waist region 19 and the second end 24 generally in or near the front crotch region 23 of the front member 12. In some aspects, as illustrated in FIGS. 1-5, the first end 22 can longitudinally oppose the second 24. As further illustrated in FIGS. 1-5, at least one of the coupling regions 20 can be positioned at or near the first end 22 and an end of the front absorbent region 16 can be positioned adjacent to the second end 24. In certain aspects, one or more of the plurality of coupling regions 20 are located within or near the front waist region 19. In some embodiments, the crotch fastener 15 can be positioned at the front crotch region 23 (e.g., along the second end 24 on the front outer layer 18), which may be generally adjacent to the front absorbent region 16. In alternative embodiments, a coupling region 20 is positioned at the front crotch region 23 (e.g., along the second end 24 on the front outer layer 18) while the crotch fastener 15 is attached or coupled to the rear crotch region 37 (e.g., along the second end 38 on the rear outer layer 32) and operable to couple to the coupling region 20 positioned in the front crotch region 23.

In some embodiments, similar to the front member 12, the rear member 14 can comprise the first end 36 generally in or near the rear waist region 33 and the second end 38 generally in or near the rear crotch region 37 of the rear member 14. In some embodiments, the first end 36 may longitudinally oppose the second end 38, as illustrated in FIGS. 1-6B. In numerous embodiments, the rear crotch region 37 releasably couples to the front crotch region 23 using at least one crotch fastener 15. In some embodiments, the second end 38 releasably couples to the second end 24 using at least one crotch fastener 15.

In some embodiments, the coupling region 20 at the first end 22 of the front member 12 can be oriented in manner substantially perpendicular to the front absorbent region 16. For example, in some aspects, the coupling region 20 can be configured and arranged to be placed over a portion of the wearer/subject to affect coupling together of the front and rear members 12, 14. By way of example only, in some embodiments, the coupling region 20 can be configured to contact an anterior portion of the hips of the wearer/subject.

In some embodiments, the coupling region 20 at the first end of the front member 12 can comprise one or more flanges 26, 26a. In various embodiments, the one or more flanges 26, 26a located in the front waist region 19. For example, the flanges 26, 26a can be comprised of laterally opposing edges of the coupling region 20 such that the flanges 26, 26a form the portions of the coupling region 20 that contact the anterior portion of the hips of the wearer/subject. As such, when viewed from a top view, the front member 12 can comprise a substantially T-like shape with the flanges 26, 26a forming the arms of the "T," as illustrated in FIGS. 1-3 and 6A-6B.

In some embodiments, the rear member 14 can comprise the plurality of coupling members 34. For example, in some aspects, the coupling members 34 can be coupled to the rear outer layer 32. In certain aspects, one or more of the plurality of coupling members 34 are located within or near the rear waist region 33. In other aspects, at least a portion of the coupling members 34 can be disposed in, at, or along any other elements of the rear member 14. In some aspects, the first end 36 of the rear member 14 may comprise a plurality of flanges 40, 40a that laterally oppose each other. In various embodiments, the flanges 40, 40a are located within the rear waist region 33. The flanges 40, 40a can be comprised of laterally opposing edges of the first end 36 such that the flanges 40, 40a form the portions of the rear member 14 that contact the posterior portion of the hips of the subject. As such, when viewed from a top view, the rear member 14 can comprise a substantially T-like shape with the flanges 40, 40a forming the arms of the "T," as illustrated in FIGS. 6A-6B. In some aspects, the flanges 40 and 40a are positioned within the rear waist region 33 and help wrap around the waist of the wearer/subject to hold the incontinence treatment system 10 in place on the waist of the wearer/subject.

In some embodiments, the rear member 14 may comprise the plurality of coupling members 34. For example, as illustrated in FIGS. 1-4, the coupling members 34 may be generally positioned at or adjacent to the first end 36 of the rear member 14. Specifically, in some aspects, the coupling members 34 may be coupled to one or more of the flanges 40, 40a. In some embodiments, the coupling members 34 may be coupled to and/or integral with the flanges 40, 40a and positioned such that the coupling members 34 laterally oppose each other. For example, in some aspects, each of the flanges 40, 40a can comprise more than one coupling member 34 and in other embodiments, each of the flanges 40, 40a may comprise a single coupling member 34. Moreover, in some embodiments, the flanges 40, 40a may comprise different numbers of coupling members 34.

In some aspects, the coupling members 34 and crotch fastener 15 can be used to couple together the front and rear members 12, 14. For example, the coupling members 34 and/or crotch fastener 15 can comprise an adhesive substance that can be used to engage other parts of the incontinence treatment system 10. Specifically, the coupling members 34 can be extended from the flanges 40, 40a (as illustrated in FIG. 1) and then when the front and rear members 12, 14 are properly positioned (as described herein), the coupling members 34 can be placed in contact with the flanges 26, 26a of the front member 12. In particular, the adhesive on the coupling members 34 can releasably bind to the flanges 26, 26a to hold together the front and rear members 12, 14 at a position substantially adjacent to the hips of the wearer/subject. In some aspects, the binding of the front and rear members 12, 14 using the coupling members 34 and the crotch fastener 15 can be releasable such that the coupling members 34 can be uncoupled from the flanges 26, 26a and the crotch fastener 15 can be uncoupled from one or both of front and rear members 12, 14 to uncouple the front and rear members 12, 14. In addition, in some embodiments, the coupling members 34 can take other configurations to couple together the front and rear members 12, 14, including, but not limited to a hook and loop configuration (e.g., VELCRO®), adhesive tape, or any other material or apparatus that is capable of coupling together the front and rear members 12, 14.

In some embodiments, in addition to comprising coupling members 34 at the first end 36 of the rear member 14, the rear crotch region 37 of the rear member 14 may comprise one or more crotch fasteners 15. For example, in some embodiments, one or more crotch fasteners 15 may be positioned (e.g., coupled to) substantially adjacent to the second end 38 of the rear member 14 (e.g., at the rear crotch region 37). In such configurations, the one or more crotch fasteners 15 positioned near the second end 38 can be used to engage and couple to the front crotch region 23 of the front member 12 (e.g., at or near the second end 24 of the front member 12). Moreover, as provided above, the one or more crotch fasteners 15 at or near the second end 38 of the rear member 14 can releasably couple the front and rear members 12, 14.

In addition, in some embodiments, additional crotch fasteners 15 can be provided that assist in coupling together the front and rear members 12, 14. For example, in some aspects, in addition to or in lieu of the crotch fastener 15 placed at the second end 38 of the rear member 14, one or more additional crotch fasteners 15 can be coupled to the second end 24 of the front member 12 to aid in coupling together the front and rear members 12, 14. In yet other embodiments, one or more unattached crotch fasteners 15 (e.g., hook and loop fastener, tape, other adhesive substance) can be coupled to both the front and rear members 12, 14 to aid in coupling together. In yet other embodiments, any combination of the aforementioned crotch fastener 15 configuration can be used to couple together the front and rear members 12, 14.

In some embodiments, the incontinence treatment system 10 can be used to provide improved sanitation and hygiene for the wearer/subject and ease of use by the wearer/subject. For example, as provided above, some embodiments of the incontinence treatment system 10 can be used to absorb and retain body exudates from wearers or subjects that are substantially or completely immobile. As such, with conventional absorbent articles, it can be physically taxing for the caregiver to regularly remove and replace when the wearer/subject has soiled him or herself. Accordingly, the methodologies provided herein can improve the patient-caregiver experience.

In some aspects, the methodology may include initially placing the rear member 14 under a posterior of a substantially or completely immobile wearer/subject. This process can be challenging because the hips and buttocks of the wearer/subject may have to be lifted to accomplish this positioning, which can be physically taxing on the caregiver.

The rear member 14 can be positioned to capture fecal material from the wearer/subject. Moreover, the rear member 14 can be positioned such that the rear waist region 33 (e.g., the first end 36) is substantially adjacent to the lower back/upper buttocks area and the flanges 40, 40a extend therefrom and are substantially adjacent to the hips. The rear absorbent region 30 can be generally positioned to adequately receive and retain feces. In addition, the coupling members 34 can be extended and ready to be coupled to the front member 12.

Next, the front member 12 can be positioned on the wearer/subject. The front member 12 can be positioned such that the front waist region 19 (e.g., the second end 24) is substantially adjacent to and/or overlaps with the rear waist region 33 of the rear member 14. For example, by overlapping the rear waist region 33 and the front waist region 19, the wearer/subject can be assured of reduced chances for leakage of fluids through the incontinence treatment system 10. One or both of the second ends 24 and 38 may be positioned below or near a transverse perineal muscle 84 of the wearer/subject. Moreover, the front absorbent region 16 can be positioned to support and/or contact the genitalia of the wearer/subject to adequately receive and retain urine or other exudates. Specifically, the support material 28 can be used to conform the front absorbent region 16 to the genitalia/crotch of the wearer/subject. Further, support material 28 can be used to conform the rear absorbent region 30 to the buttocks of the wearer/subject. In addition, the first end 22 can be positioned adjacent to the anterior pelvis of the wearer/subject and the flanges 26, 26a can extend therefrom in a lateral direction. Once in place, the crotch fastener 15 can couple the front crotch region 23 to the rear crotch region 37 to hold together the front and rear members 12, 14. At such time, the incontinence treatment system 10 has been positioned on the wearer/subject such that the front and rear members 12, 14 are held together by the coupling members 34 and crotch fastener 15 and form a seam along the sides of the wearer/subject.

Thereafter, some portions of the incontinence treatment system 10 can be removed as necessary. For example, when the wearer/subject voids his or her bladder, the front absorbent region 16 will become soiled and the front member 12 will be removed by the caregiver. However, because the front member 12 and the front absorbent region 16 are separate from the rear member 14 and the rear absorbent region 30, there is no need to change the rear member 14 unless the rear member 14 has otherwise become soiled. As such, it makes it much easier and less taxing for the caregiver to have to only change the front member 12 because there is no need to experience the lifting and maneuvering necessary to change the rear member 14. Specifically, some wearers/subjects may experience removal and replacement of the front member 12 at an increased rate, simply because of the ease through which a caregiver can change the front member 12. For example, some caregivers may change the front member 12 three to six times as often as a conventional absorbent article.

Moreover, because the wearer/subject is more likely to urinate more often than experience a bowel movement, the rear member 14 will, in general, be changed less often. However, when the wearer/subject does experience a bowel movement or the rear member 14 otherwise becomes soiled, the rear member 14 can be separately changed if desired.

Furthermore, due to more frequent removal and replacement of the front member 12, one of ordinary skill in the art would recognize that the wearer/subject should experience an improvement in skin quality around the incontinence treatment system 10. Specifically, the longer a soiled conventional absorbent article remains in contact with the skin of a wearer/subject, the greater the risk that the wearer/subject will experience incontinence-associated dermatitis (e.g., skin breakdown), which can lead to infection. Thus, more frequent skin care and incontinence care (e.g., by frequently removing a soiled front member 12) likely will lead to a lower incidence of skin breakdown (e.g., incontinence associated dermatitis) and infection for the wearer/subject. As such, by enabling more simple and less strenuous avenues for removing and replacing just the front member 12, embodiments of the incontinence treatment system 10 provide significant improvements over existing absorbent articles.

In addition, in some embodiments, the incontinence treatment system 10 can be packaged for use in different configurations. For example, because the front and rear members 12, 14 are separate elements, different numbers of front and rear members 12, 14 can be provided in commercial packaging. As mentioned above, it is expected that the front member 12 will have to be removed and replaced more often than the rear member 14 due to the increased frequency of urination, relative to defecation. As such, it may be beneficial to include more front member 12 units in a given commercial package, relative to rear member 14 units. Specifically, there could be 2, 3, 4, 5, 6, 7, 8, 9, or 10 or more front member 12 units in a given package per each rear member 14 unit included in the same package. As such, there is not an excess of rear member 14 units included in a given commercial package.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of using an incontinence system on a subject, the method comprising:
    providing a rear incontinence member comprising a rear absorbent region, a rear outer layer coupled to the rear absorbent region, a rear waist region, and a crotch region of the rear incontinence member;
    providing a front incontinence member comprising a front absorbent region, a front outer layer coupled to the front absorbent region, a front waist region, and a crotch region of the front incontinence member;
    providing a crotch fastener operable to releasably couple the front crotch region of the front incontinence member to the rear crotch region of the rear incontinence member;
    positioning the rear incontinence member on the subject so that the rear absorbent region is adjacent to a posterior of the subject and the rear waist region is substantially adjacent to hips of the subject with the rear crotch region positioned near or covering a transverse perineal muscle of the subject;
    positioning the front incontinence member on the subject so that the front absorbent region covers the urethra of the subject and the front waist region is substantially adjacent to the hips of the subject, wherein the rear crotch region overlaps the front crotch region with the overlapped portion of the front crotch region being between the rear crotch region and the subject;
    coupling together the front crotch region to the rear crotch region by using the crotch fastener;

uncoupling the front crotch region from the rear crotch region;
discarding the front incontinence member; and
recoupling a new front incontinence member to the already positioned rear incontinence member.

2. The method of claim 1, wherein the rear incontinence member further comprises a rear waist region having a left side and a right side and the front incontinence member further comprises a front waist region having a left side and a right side, the method further comprising:
providing a right side waist coupler operable to releasably couple the right side of the rear waist region to the right side of the front waist region;
providing a left side waist coupler operable to releasably couple the left side of the rear waist region to the left side of the front waist region;
coupling the right side of the rear waist region to the right side of the front waist region by using the right side waist coupler; and
coupling the left side of the rear waist region to the left side of the front waist region by using the left side waist coupler.

3. The method of claim 1, further comprising uncoupling the front and rear incontinence members when the subject has a bowel movement, discarding the rear incontinence member, and positioning an unsoiled rear incontinence member on the subject and coupling the rear incontinence member to the front incontinence member.

4. The method of claim 1, wherein the subject is a patient and the front incontinence member comprises a support material being disposed around at least a portion of the front absorbent region, and wherein the support material comprises elastic.

5. The method of claim 1, wherein the front incontinence member is the same shape and size as the rear incontinence member.

6. The method of claim 1, wherein the rear crotch region overlaps the front crotch region by at least 2 cm with the overlapped portion of the front crotch region being adjacent to the skin of the subject.

7. The method of claim 1, wherein the crotch fastener is coupled to the front crotch region and the rear crotch region abuts the crotch fastener, thereby operating as a barrier to define the amount the rear crotch region overlaps the front crotch region when the crotch fastener is coupled to the rear crotch region.

8. An incontinence treatment system comprising:
a rear incontinence member comprising a rear absorbent region having a rear absorbent material, a rear outer layer coupled to the rear absorbent region, a rear waist region having at least one rear waist coupler, and a rear crotch region of the rear incontinence member;
a front incontinence member comprising a front absorbent region having a front absorbent material, a front outer layer coupled to the front absorbent region, a front waist region having at least one front waist coupler, and a front crotch region of the front incontinence member; and
a crotch fastener operable to releasably couple the front crotch region of the front incontinence member to the rear crotch region of the rear incontinence member;
wherein, when the incontinence treatment system is worn by a subject and the front crotch region is coupled to the rear crotch region, the rear crotch region overlaps the front crotch region with the overlapped portion of the front crotch region being between the rear crotch region and the subject.

9. An incontinence treatment system, comprising:
a front incontinence member having a front waist region, a front crotch region, and a front absorbent region having a front absorbent material;
a rear incontinence member having a rear waist region, a rear crotch region, and a rear absorbent region having a rear absorbent material;
a first waist coupler operable to releasably couple a left portion of the front waist region to a left portion of the rear waist region;
a second waist coupler operable to releasably couple a right portion of the front waist region to a right portion of the rear waist region; and
a crotch fastener operable to releasably couple the front crotch region of the front incontinence member to the rear crotch region of the rear incontinence member;
wherein the front incontinence member is configured to be uncoupled from the rear incontinence member, discarded, and replaced by a new front incontinence member.

10. The incontinence treatment system of claim 9, wherein each of the rear outer layer and the front outer layer comprise one or more hydrophobic materials and:
the rear absorbent region further comprises a rear liquid-permeable layer such that at least half of the rear absorbent material is sandwiched between the rear liquid-permeable layer and the rear outer layer;
the front absorbent region further comprises a front liquid-permeable layer such that at least half of the front absorbent material is sandwiched between the front liquid-permeable layer and the front outer layer; and
each of the rear liquid-permeable layer and front liquid-permeable layer is adapted to contact the skin of a subject.

11. The incontinence treatment system of claim 9, wherein at least one of the rear absorbent material or the front absorbent material comprises at least two layers of hydrophilic material.

12. The incontinence treatment system of claim 9, further comprising:
a hydrophobic dam surrounding at least two sidewalls of the front absorbent material in the front crotch region, or
a hydrophobic dam surrounding at least three sidewalls of the front absorbent material, the hydrophobic dam extending beyond the front crotch region towards the front waist region.

13. The incontinence treatment system of claim 9, wherein the incontinence treatment system has a shape selected from the group consisting of: rectangular, hourglass, and U-shape, and/or the front crotch region is elasticized to contour the front crotch region to a subject's anatomy.

14. The incontinence treatment system of claim 9, further comprising:
a support material being disposed around at least a portion of the front absorbent region wherein the support material is positioned within the front incontinence member, thereby positioning the front absorbent region adjacent to a urogenital anatomy of a subject, and the support material comprises an elastomer.

15. The incontinence treatment system of claim 9, wherein the front incontinence member is positioned adjacent to a urogenital anatomy of a subject and the rear incontinence member is positioned adjacent to a posterior of the subject.

16. The incontinence treatment system of claim 9, wherein the front incontinence member is the same shape and size as the rear incontinence member and the front incontinence member is interchangeable with the rear incontinence member.

17. The incontinence treatment system of claim 9, wherein, when the incontinence treatment system is worn by a subject and the front crotch region is coupled to the rear crotch region, the rear crotch region overlaps the front crotch region by at least 2 cm with the overlapped portion of the front crotch region being between the rear crotch region and a subject.

18. The incontinence treatment system of claim 9, wherein the crotch fastener is coupled to the front crotch region and the rear crotch region abuts the crotch fastener, thereby operating as a barrier to define the amount the rear crotch region overlaps the front crotch region when the crotch fastener is coupled to the rear crotch region.

19. The incontinence treatment system of claim 9, wherein the rear incontinence member is positioned with the rear crotch region positioned near or covering a transverse perineal muscle of a subject; and/or wherein the rear absorbent layer is omitted from the first 1.5 cm of side edges of the rear crotch region.

* * * * *